(12) United States Patent
Leonhardt et al.

(10) Patent No.: US 7,686,799 B2
(45) Date of Patent: Mar. 30, 2010

(54) DEPLOYMENT SYSTEM FOR MYOCARDIAL CELLULAR MATERIAL

(75) Inventors: Howard J Leonhardt, Weston, FL (US); Robert D Lashinski, Sebastopol, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1178 days.

(21) Appl. No.: 10/332,737

(22) PCT Filed: Jul. 13, 2001

(86) PCT No.: PCT/US01/22029

§ 371 (c)(1),
(2), (4) Date: Jul. 15, 2003

(87) PCT Pub. No.: WO02/05866

PCT Pub. Date: Jan. 24, 2002

(65) Prior Publication Data

US 2004/0010231 A1 Jan. 15, 2004

Related U.S. Application Data

(60) Provisional application No. 60/217,976, filed on Jul. 13, 2000, provisional application No. 60/217,977, filed on Jul. 13, 2000, provisional application No. 60/253,514, filed on Nov. 28, 2000.

(51) Int. Cl.
*A61M 31/00* (2006.01)
(52) U.S. Cl. .......................... 604/507; 604/59; 604/60; 604/164.01; 604/264; 600/7; 600/8; 623/8

(58) Field of Classification Search ................... 604/57, 604/59–61, 164.01, 264, 507, 170.03, 121; 600/7–8; 623/8
See application file for complete search history.

(56) References Cited

U.S. PATENT DOCUMENTS 1,162,901 A 12/1915 Cantry et al.

(Continued)

FOREIGN PATENT DOCUMENTS

DE 44 20 232 A1 12/1995

(Continued)

OTHER PUBLICATIONS

A Collection of Abstracts, Society of Thoracic Surgeons, 1999.

(Continued)

*Primary Examiner*—Nicholas D Lucchesi
*Assistant Examiner*—Quynh-Nhu H Vu
(74) *Attorney, Agent, or Firm*—Blakely, Sokoloff, Taylor & Zafman LLP

(57) ABSTRACT

A catheter-based deployment system for deploying cellular material (22) into the heart muscle (25). The deployment system includes a guiding catheter (19) and a needle assembly (31) capable of sliding within the guiding catheter. The needle assembly (31) terminates in a tip (34) having at least one side with an opening (43) in communication with a lumen (20) disposed within the needle assembly (31). Once the guiding catheter (19) is positioned the needle assembly (31) is advanced until the tip (34) penetrates the muscle wall (25). At a predetermined depth the cellular material (22) may be deployed into the muscle wall (25) via a push rod (46) disposed through the lumen of the needle assembly (31).

12 Claims, 5 Drawing Sheets

U.S. PATENT DOCUMENTS

| | | |
|---|---|---|
| 2,001,638 A | 5/1935 | Gustaf |
| 2,710,000 A | 6/1955 | Cromer et al. |
| 2,749,909 A | 6/1956 | Ullery et al. |
| 3,120,845 A | 2/1964 | Horner |
| 3,477,423 A | 11/1969 | Griffith et al. |
| 3,557,794 A | 1/1971 | Van Patten |
| 3,614,953 A | 10/1971 | Moss |
| 3,692,020 A | 9/1972 | Schied |
| 3,780,246 A | 12/1973 | Beckering et al. |
| 4,186,750 A | 2/1980 | Patel |
| 4,207,874 A | 6/1980 | Conley et al. |
| 4,299,230 A | 11/1981 | Kubota |
| 4,356,826 A | 11/1982 | Kubota |
| 4,362,161 A | 12/1982 | Reimels et al. |
| 4,381,037 A | 4/1983 | Cuneo |
| 4,461,305 A | 7/1984 | Cibley |
| 4,479,896 A | 10/1984 | Antoniades |
| 4,576,162 A | 3/1986 | McCorkle |
| 4,578,057 A | 3/1986 | Sussman |
| 4,578,061 A * | 3/1986 | Lemelson ............... 604/170.01 |
| 4,582,056 A | 4/1986 | McCorkle, Jr. |
| 4,596,574 A | 6/1986 | Urist |
| 4,600,014 A | 7/1986 | Beraha |
| 4,640,296 A | 2/1987 | Schnepp-Pesch et al. |
| 4,646,738 A | 3/1987 | Trott |
| 4,702,261 A | 10/1987 | Cornell et al. |
| 4,729,763 A | 3/1988 | Henrie |
| 4,788,975 A | 12/1988 | Shturman et al. |
| 4,790,812 A | 12/1988 | Hawkins, Jr. et al. |
| 4,792,327 A | 12/1988 | Swartz |
| 4,813,930 A | 3/1989 | Elliott |
| 4,850,354 A | 7/1989 | McGurk-Barleson et al. |
| 4,895,166 A | 1/1990 | Farr et al. |
| 4,898,577 A | 2/1990 | Badger et al. |
| 4,917,102 A | 4/1990 | Miller et al. |
| 4,923,462 A | 5/1990 | Stevens |
| RE33,258 E | 7/1990 | Onik et al. |
| 4,957,742 A | 9/1990 | Knighton |
| 4,964,854 A * | 10/1990 | Luther ................... 604/166.01 |
| 4,976,710 A | 12/1990 | Mackin |
| 4,985,028 A | 1/1991 | Isner et al. |
| 5,030,201 A | 7/1991 | Palestrant |
| 5,093,877 A | 3/1992 | Aita et al. |
| 5,104,393 A | 4/1992 | Isner et al. |
| 5,106,386 A | 4/1992 | Isner et al. |
| 5,123,904 A | 6/1992 | Shimomura et al. |
| 5,125,924 A | 6/1992 | Rudko |
| 5,125,926 A | 6/1992 | Rudko |
| 5,133,713 A | 7/1992 | Huang et al. |
| 5,135,531 A | 8/1992 | Shiber |
| 5,152,744 A | 10/1992 | Krause et al. |
| 5,195,988 A | 3/1993 | Haaga |
| 5,224,951 A | 7/1993 | Freitas |
| 5,242,460 A | 9/1993 | Klein et al. |
| 5,263,959 A | 11/1993 | Fischell |
| 5,269,785 A | 12/1993 | Bonutti |
| 5,273,051 A | 12/1993 | Wilk |
| 5,279,567 A | 1/1994 | Ciaglia et al. |
| 5,281,218 A | 1/1994 | Irman |
| 5,285,795 A | 2/1994 | Ryan |
| 5,313,949 A | 5/1994 | Yock et al. |
| 5,323,781 A | 6/1994 | Ideker et al. |
| 5,324,284 A | 6/1994 | Irman |
| 5,330,466 A | 7/1994 | Irman |
| 5,336,237 A | 8/1994 | Chin et al. |
| 5,339,799 A | 8/1994 | Kami et al. |
| 5,342,300 A | 8/1994 | Stefanadis et al. |
| 5,342,393 A | 8/1994 | Stack |
| 5,354,310 A | 10/1994 | Garnic |
| 5,358,472 A | 10/1994 | Vance |
| 5,358,485 A | 10/1994 | Vance |
| 5,366,468 A | 11/1994 | Fucci et al. |
| 5,379,772 A | 1/1995 | Irman |
| 5,380,316 A | 1/1995 | Aita et al. |
| 5,383,884 A | 1/1995 | Summers |
| 5,389,073 A | 2/1995 | Imran |
| 5,389,096 A | 2/1995 | Aita et al. |
| 5,392,917 A | 2/1995 | Alpern et al. |
| 5,403,334 A | 4/1995 | Evans et al. |
| 5,409,000 A | 4/1995 | Imran |
| 5,415,166 A | 5/1995 | Imran |
| 5,419,777 A * | 5/1995 | Hofling ....................... 604/264 |
| 5,421,821 A | 6/1995 | Janicki et al. |
| 5,425,376 A * | 6/1995 | Banys et al. ................. 600/566 |
| 5,429,144 A | 7/1995 | Wilk |
| 5,439,474 A | 8/1995 | Li |
| 5,443,443 A | 8/1995 | Shiber |
| 5,454,791 A | 10/1995 | Tovey et al. |
| 5,456,689 A | 10/1995 | Kresch et al. |
| 5,464,395 A | 11/1995 | Faxon et al. |
| 5,465,717 A | 11/1995 | Imran |
| 5,470,316 A | 11/1995 | Tovey et al. |
| 5,488,958 A | 2/1996 | Topel et al. |
| 5,492,119 A | 2/1996 | Abrams |
| 5,496,273 A | 3/1996 | Pastrone et al. |
| 5,497,784 A | 3/1996 | Imran |
| 5,505,725 A | 4/1996 | Samson |
| 5,507,802 A | 4/1996 | Imran |
| 5,520,634 A | 5/1996 | Fox et al. |
| 5,527,279 A | 6/1996 | Imran |
| 5,531,780 A | 7/1996 | Vachon |
| 5,551,427 A * | 9/1996 | Altman ....................... 600/374 |
| 5,554,152 A | 9/1996 | Aita |
| 5,562,694 A | 10/1996 | Sauer |
| 5,569,178 A | 10/1996 | Henry |
| 5,569,254 A | 10/1996 | Carson et al. |
| 5,569,284 A | 10/1996 | Young et al. |
| 5,571,133 A | 11/1996 | Yoon |
| 5,575,772 A | 11/1996 | Lennox |
| 5,575,787 A | 11/1996 | Abela et al. |
| 5,575,810 A | 11/1996 | Swanson |
| 5,578,067 A | 11/1996 | Ekwall et al. |
| 5,584,842 A | 12/1996 | Fogarty et al. |
| 5,591,159 A | 1/1997 | Taheri |
| 5,601,573 A | 2/1997 | Fogelbert et al. |
| 5,601,586 A | 2/1997 | Fucci et al. |
| 5,601,588 A | 2/1997 | Tonomura et al. |
| 5,606,974 A | 3/1997 | Castellano et al. |
| 5,607,421 A | 3/1997 | Jeevanandam et al. |
| 5,609,591 A | 3/1997 | Daikuzono |
| 5,609,621 A | 3/1997 | Bonner |
| 5,611,803 A | 3/1997 | Heaven et al. |
| 5,613,972 A | 3/1997 | Lee et al. |
| 5,640,955 A | 6/1997 | Ockuly et al. |
| 5,643,253 A | 7/1997 | Baxter et al. |
| 5,649,911 A | 7/1997 | Trerotola |
| 5,651,781 A | 7/1997 | Grace |
| 5,656,339 A | 8/1997 | Wesseling et al. |
| 5,658,263 A | 8/1997 | Dang et al. |
| 5,662,124 A | 9/1997 | Wilk |
| 5,662,671 A | 9/1997 | Barbut et al. |
| 5,669,920 A | 9/1997 | Conley et al. |
| 5,683,362 A | 11/1997 | Rowland et al. |
| 5,688,234 A | 11/1997 | Frisbie |
| 5,702,412 A | 12/1997 | Popov et al. |
| 5,709,697 A | 1/1998 | Ratcliff et al. |
| 5,722,400 A | 3/1998 | Ockuly et al. |
| 5,724,975 A | 3/1998 | Negus et al. |
| 5,725,521 A | 3/1998 | Mueller |
| 5,730,741 A | 3/1998 | Horzewski et al. |
| 5,743,870 A | 4/1998 | Edwards |
| 5,746,713 A | 5/1998 | Hood et al. |
| 5,776,092 A | 7/1998 | Farin et al. |
| 5,782,823 A | 7/1998 | Mueller |

| | | |
|---|---|---|
| 5,797,870 A | 8/1998 | March et al. |
| 5,807,384 A | 9/1998 | Mueller |
| 5,814,028 A | 9/1998 | Swartz et al. |
| 5,830,210 A | 11/1998 | Rudko et al. |
| 5,830,222 A | 11/1998 | Makower |
| 5,833,715 A | 11/1998 | Vachon et al. |
| 5,834,418 A | 11/1998 | Brazeau et al. |
| 5,840,059 A | 11/1998 | March et al. |
| 5,846,225 A | 12/1998 | Rosengart et al. |
| 5,857,995 A | 1/1999 | Thomas et al. |
| 5,871,495 A | 2/1999 | Mueller |
| 5,873,366 A | 2/1999 | Chim et al. |
| 5,876,373 A | 3/1999 | Giba et al. |
| 5,878,751 A * | 3/1999 | Hussein et al. ............... 128/898 |
| 5,885,272 A | 3/1999 | Aita et al. |
| 5,885,276 A | 3/1999 | Ammar et al. |
| 5,893,848 A | 4/1999 | Negus et al. |
| 5,899,874 A | 5/1999 | Jonsson |
| 5,906,594 A | 5/1999 | Scarfone et al. |
| 5,910,150 A | 6/1999 | Saadat |
| 5,916,214 A | 6/1999 | Cosio et al. |
| 5,921,982 A | 7/1999 | Lesh et al. |
| 5,928,943 A | 7/1999 | Franz et al. |
| 5,938,632 A | 8/1999 | Ellis |
| 5,941,868 A | 8/1999 | Kaplan et al. |
| 5,941,893 A | 8/1999 | Saadat |
| 5,944,716 A | 8/1999 | Hektner |
| 5,951,567 A | 9/1999 | Javier, Jr. et al. |
| 5,954,701 A | 9/1999 | Matalon |
| 5,964,754 A | 10/1999 | Osypka |
| 5,964,757 A | 10/1999 | Ponzi |
| 5,968,059 A | 10/1999 | Ellis et al. |
| 5,971,993 A | 10/1999 | Hussei et al. |
| 5,980,545 A | 11/1999 | Pacala et al. |
| 5,989,278 A | 11/1999 | Mueller |
| 6,004,302 A * | 12/1999 | Brierley ....................... 604/264 |
| 6,030,377 A * | 2/2000 | Linhares et al. ................ 606/7 |
| 6,036,677 A | 3/2000 | Javier, Jr. et al. |
| 6,045,530 A | 4/2000 | Krueger et al. |
| 6,045,565 A | 4/2000 | Ellis et al. |
| 6,051,008 A | 4/2000 | Saadat et al. |
| 6,056,743 A | 5/2000 | Ellis et al. |
| 6,066,126 A | 5/2000 | Li et al. |
| 6,093,177 A | 7/2000 | Javier, Jr. et al. |
| 6,102,887 A * | 8/2000 | Altman ....................... 604/22 |
| 6,102,926 A | 8/2000 | Saadat et al. |
| 6,106,520 A | 8/2000 | Laufer et al. |
| 6,120,520 A | 9/2000 | Saadat et al. |
| 6,126,654 A | 10/2000 | Giba et al. |
| 6,162,202 A | 12/2000 | Sicurelli et al. |
| 6,165,164 A | 12/2000 | Hill et al. |
| 6,179,809 B1 | 1/2001 | Khairkhahan et al. |
| 6,217,554 B1 | 4/2001 | Green |
| 6,224,584 B1 | 5/2001 | March et al. |
| 6,238,389 B1 | 5/2001 | Paddock et al. |
| 6,251,079 B1 | 6/2001 | Gambale et al. |
| 6,251,104 B1 | 6/2001 | Kesten et al. |
| 6,254,573 B1 | 7/2001 | Haim et al. |
| 6,270,496 B1 | 8/2001 | Bowe et al. |
| 6,283,951 B1 | 9/2001 | Flaherty et al. |
| 6,302,870 B1 | 10/2001 | Jacobsen et al. |
| 6,309,370 B1 | 10/2001 | Haim et al. |
| 6,322,548 B1 | 11/2001 | Payne et al. |
| 6,391,005 B1 | 5/2002 | Lum et al. |
| 6,405,091 B1 * | 6/2002 | Vachon et al. ............... 607/120 |
| 6,432,126 B1 * | 8/2002 | Gambale et al. ............. 623/1.1 |
| 6,494,862 B1 | 12/2002 | Ray et al. |
| 6,517,521 B1 | 2/2003 | Ly |
| 6,546,787 B1 | 4/2003 | Schiller et al. |
| 6,613,062 B1 | 9/2003 | Leckrone et al. |
| 6,620,139 B1 * | 9/2003 | Plicchi et al. ............... 604/264 |
| 6,638,233 B2 | 10/2003 | Corvi et al. |
| 6,905,476 B2 | 6/2005 | Ponzi |
| 7,094,201 B1 * | 8/2006 | Stokes et al. ................ 600/120 |
| 2003/0083686 A1 | 5/2003 | Freeman et al. |
| 2004/0092893 A1 | 5/2004 | Haider et al. |
| 2004/0171933 A1 | 9/2004 | Stoller et al. |
| 2005/0027199 A1 | 2/2005 | Clarke |

FOREIGN PATENT DOCUMENTS

| | | |
|---|---|---|
| EP | 0807412 | 11/1997 |
| EP | 0853921 | 7/1998 |
| EP | 0868923 | 7/1998 |
| EP | 0876796 | 11/1998 |
| EP | 0895752 | 10/1999 |
| WO | WO 86/03122 | 6/1986 |
| WO | WO 8803035 A2 * | 5/1988 |
| WO | WO 96/25097 | 8/1996 |
| WO | WO 96/26675 | 9/1996 |
| WO | WO 96/35469 | 11/1996 |
| WO | WO 97/10753 | 3/1997 |
| WO | WO 97/13471 | 4/1997 |
| WO | WO 98/05307 | 2/1998 |
| WO | WO 98/17186 | 4/1998 |
| WO | WO 98/38916 | 9/1998 |
| WO | WO 98/39045 | 9/1998 |

OTHER PUBLICATIONS

Assmus, Tranplantation of Progenitor Cells and Regeneration Enhancement in Acute Myocardial Infarction (TOPCARE-AMI), Clinical Investigation and Reports, Oct. 8, 2002, pp. 3009-3017, Department of Molecular Cardiology and Department of Hematology (H.M., D.H.) University of Frankfurt, Frankfurt, Germany, Circulation available at http://www.circulationha.org DOI: 10.1161/01.CIR.0000043246.74879CD.

Chapter 1 PCT International Preliminary Report (IPER) for PCT Application No. PCT/US2004/027961. Mailed on Mar. 16, 2006 (9 pages).

Cooley, Denton A., M.D. et al., "Transmyocardial Laser Revascularization: Clinical Experience with Twelve-Month Follow-Up," The Journal of Thoracic and Cardiovascular Surgery, (Apr. 1996), pp. 791-799.

Cooley, Denton A., M.D., et al., "Transmyocardial Laser Revascularization: Anatomic Evidence of Long=Term Channel Patency," Texas heart institute Journal, vol. 21, No. 3 (1994), pp. 220-224.

Fenton II, John W. et al. "Thrombin and Antithrombotics," Seminars in Thrombosis and Hemostasis, vol. 24, No. 2, 1998, pp. 1987-1991.

Frazier, O.H., M.D., "Myocardial Revascularization with Laser: Preliminary Findings," Supplement II Circulation, vol. 92, No. 9, (Nov. 1995), pp. II-58-II-65.

Hardy, Roger Ian, "A Histological Study of Laser-Induced Transmyocardial Channels," Lasers in Surgery and Medicine, (1997), pp. 6:563-573.

Henry, Timothy D., Can We Really Grow New Blood Vessels, The Lancet, vol. 351, Jun. 20, 1998, pp. 1926-1827.

Hershey, John E. et al., "Transmyocardial Puncture Revascularization: A possible Emergency Adjunct to Arterial Implant Surgery," Geriatrics (Mar. 1969), pp. 101-108.

Horvath, Keith A. M.D., et al., "Recovery and Viability of an Acute Myocardial Infarct After Transmyocardial Laser Revascularization," Journal of American College of Cardiology, vol. 25, No. 1 (Jan. 1995), pp. 258-263.

Horvath, Keith A. M.D., et al., "Transmyocardial Laser Revascularization: Operative Techniques and Clinical Results at Two Years," The Journal of Thoracic and Cardiovascular Surgery, (May 1996) pp. 1047-1053.

Khazei, Hassan A., "A New Method of Myocardial Revascularization," The Annals of Thoracic Surgery, vol. 6, No. 2, (Aug. 1968) pp. 163-171.

Knighton, David R., et al., "Role of Platelets and Fibrin in the Healing Sequence," Annals of Surgery, vol. 196, No. 4, Oct. 1982, pp. 379-388.

Kohmoto, Takushi, M.D., "Does Blood Flow Through Holmium: YAG Transmyocardial Laser Channels?," Ann. Thorac. Surg., (1996) pp. 61: 861-868.

Kuzela, Ladislaw, "Experimental Evaluation of Direct Transventricular Revascularization," Journal of Thoracic and Cardiovascular Surgery, vol. 57, No. 6, (June 1969), pp. 770-773.

Lee, Garrett, M.D. "Effects of Laser Irradiation Delivered by Flexible Fiberoptic System on the Left Ventricular Internal Myocardium," American Heart Journal, (Sep. 1983) pp. 587-590.

Losordo, Douglas, W., et al., "Gene Therapy for Mycardial Angiogenesis Initial Clinical Results with Direct Myocardial Injection of phVEGF 165 as Sole Therapy Myocardial Ischemia," Circulation, 1998, 98:2800-2804.

Maloney, James P. et al., "In Vitro Release of Vascular Endothelial Growth Factor During Platelet Aggregation," American Physiological Society, H1054-H1061, 1998.

Mandrusov, Membrane-Based Cell Affinity Chromatography to Retrieve Viable Cells, Biotechnol, Prob. 1995, 11, 208-213, Artificial Organs Research Laboratory, Department of Chemical Engineering, Material Sciences and Metallurgy, Columbia University, New York, New York 10027, and Lousville, Lousville, Kentucky 40292.-Abstract.

Miyazono, Kohei et al, "Platelet-Derived Endothelial Cell Growth Factor," Progress in Growth Factor Research, vol. 3, 1991, pp. 207-217.

NASA's Jet Propulsion Laboratory, "Swivel-head Sampling Drill Bit," NASA Tech Briefs, Nov. 1998.

PCT Communication—Supplementary European Search Report, Aug. 3, 2001, 3 pages.

PCT International Search Report Mar. 18, 1998, 4 pages.

PCT Notification of Transmittal of International Preliminary Examination Report, Apr. 15, 1999, 13 pages.

PCT Search Report dated Dec. 16, 2004, 8 pages.

PCT Written Opinion, Dec. 23, 1998, 4 pages.

Pipili-Synetos, E. et al., "Evidence That Platelets Promote Tube Formation by Endothelial Cells on Matrigel," British Journal of Pharmacology, vol. 125, 1998, pp. 1252-1257.

PMR Product, Axcis tm PMR. System, http://www.cardiogenesis.com/percutaneous/product.html, Jan. 27, 1999.

Sen, P.K., et al. "Further Studies in Multiple Transmyocardial Acupuncture as a Method of Myocardial Revascularization," Surgery, Vo. 64, No. 5, (Nov. 1968), pp. 861-870.

Simons, Michael et al. "Food for Starving Hearts," Nature Medicine, vol. 2 No. 5, May 1996, pp. 519-520.

Thaning, Otto, "Transmyocardial Laser Revascularization in South Africa," SAMJ, vol. 85, No. 8 (Aug. 1995) pp. 787-788.

The PMR™ Procedure,: http://www.cardiogenesis.com; percutaneous/procedure.html, Jan. 27, 1999.

Tsopanoglou, Nikos E. et al., "Thrombin Promotes Angiogenesis By a Mechanism Independent of Fibrin Formation," American Physiological Society, 0363-6143/93, C1302-1307.

Van Oppell, Ulrich O., "Transmyocardial Laser Revascularization," SAMJ, vol. 85, No. 9, (Sep. 1995), p. 930.

Verheul, Henk M. W., et al., "Platelet: Transporter of Vascular Endothelial Growth Factor," Clinical Cancer Research, vol. 3, Dec. 1997, pp. 2187-2190.

Wakabayashi, Akio, "Myocardial Boring for the Ischemic Heart," Arch. Surgery, vol. 95, (Nov. 1967), pp. 743-752.

Wartiovaara, Ulla et al., Peripheral Blood Platelets Express VEGF-C and VEGF Which are Released During Platelet Activation, Thromb Haemost, 9198, 80:171-5.

Washington Adventist Hospital, "Washington Area Cardiologist Performs First State-of-the Art Heart Procedure in U.S.," PR newswire, Dec. 15, 1999, 2 pages.

White, Manuel et al., "Multiple Transmyocardial Puncture Revascularization in Refractory ventricular Fibrillation due to Myocardial Ischemia," The Annals of Thoracic Surgery, vol. 6, No. 6, (Dec. 1968), pp. 557-563.

Folkman, Judah. "Angiogenic Therapy of the Human Heart," *Circulation*, 97:628-629, (1998).

\* cited by examiner

DEPLOYMENT SYSTEM FOR MYOCARDIAL CELLULAR MATERIAL

CROSS-REFERENCE TO RELATED APPLICATION

The present application claims priority to U.S. Provisional Patent Application No. 60/253,514 entitled "Myocardial Cellular Material and Deployment System Therefor," filed on Nov. 28, 2000; to U.S. Provisional Patent Application No. 60/217,976 entitled "Myocardial Cellular Pellet and Deployment System Therefor," filed on Jul. 13, 2000; and U.S. Provisional Patent Application No. 60/217,977 entitled "Myocardial Cellular Material and Porous Ceramic Delivery System Therefor," filed on Jul. 13, 2000, all of which are hereby incorporated by reference.

FIELD OF INVENTION

The present invention pertains generally to cellular based implants for heart muscle tissue and specifically to a deployment system for myocardial cellular materials.

BACKGROUND OF THE INVENTION

Coronary heart disease is one of the leading causes of death in the United States. Heart attacks or myocardial infarctions caused by coronary heart disease can cause immediate death or can cause significant morbidity rates due to irreversible damage to the heart, such as scarring of the myocardial tissue.

Following a myocardial infarction there is always a certain time period of non-perfusion during which ischemia may develop. This is especially true during the patient transport to the hospital and until occluded vessels can be reopened by percutaneous transluminal coronary angioplasty (PTCA) or thrombolytic agents, for example. Thrombolytic agents, administered either intravenously or directly into the coronary arteries, work by dissolving the occluding thrombus and thereby reestablishing blood flow. When thrombolytic agents are administered properly, they can be expected to restore blood flow relatively quickly in cases of minor myocardial infarctions. However, in cases of massive myocardial infarctions, or in cases of delayed administration, the efficacy of the agents can be drastically reduced.

In situations where heart muscle damage has occurred due to myocardial infarctions or coronary heart disease, there have been attempts at improving perfusion in the damaged heart muscle and at repairing the heart muscle damage.

Some of the treatments have included attempts at growing microvessels through angiogenesis techniques. These techniques have experienced some significant drawbacks. The vessels that have been grown by these techniques have generally been too small in diameter and have provided little perfusion to the distant areas of the heart muscle, where perfusion is most needed. Also, most previous attempts such as U.S. Pat. No. 5,941,868 issued to Kaplan et al. involved injecting growth factors into the bloodstream in the target area which resulted in limited uptake into the heart muscle. These designs were at best only able to relieve symptoms of angina but provided no improvement of cardiac function and were not able to convert dead muscle area into working muscle.

Some of the treatments for revascularizing the myocardium have involved the creation of channels within the myocardium for providing oxygenated blood to myocardial cells without requiring coronary circulation.

U.S. Pat. No. 5,878,751 issued to Hussein et al. discloses stent and needle means for creating and maintaining a patent lumen in the diseased myocardium. The stent is carried into the myocardium through the heart wall on the outside of a needle and then the needle is withdrawn through the center of the stent.

U.S. Pat. No. 5,972,013 issued to Schmidt discloses a pericardial access device having a penetrating body axially mobile with the lumen of a guide tube. The guide tube includes a deflecting mechanism for deflecting the distal end of the penetrating body. In use, a patient's pericardium is contacted with the distal end of the guide tube and suction is applied to form a pericardial bleb. The penetrating body is axially mobilized distally within the lumen of the guide tube until the deflecting mechanism deflects the penetrating body to cause the penetrating end of the penetrating body to enter the bleb of the pericardial tissue at an angle oblique to the longitudinal axis of the guide tube.

Accordingly, what is needed is a catheter-based deployment system for introducing myocardial cellular materials into the heart wall in a minimally invasive procedure.

SUMMARY OF THE INVENTION

The present invention meets the above described need by providing a system for deploying myocardial cellular materials directly into the heart muscle.

The present invention provides a deployment system for a cellular material in a solid, paste or slurry form that is comprised of a combination of cellular materials and pharmacological materials that are implanted directly into the heart muscle. The cellular materials may also be provided and delivered to the heart muscle in liquid form.

The deployment system for the present invention includes a guiding catheter and a slidable injection needle assembly for delivering the cellular materials. The needle assembly is capable of being pushed into and through the heart wall by a mechanism attached to the needle assembly and capable of being manipulated by the interventionist.

The needle assembly has a central lumen with a push rod and a platform for positioning the cellular material disposed therein. The central lumen terminates at an opening in the side of the tip of the needle assembly. Once the tip of the needle assembly is advanced into the myocardium a predetermined distance, the cellular material can be ejected from the needle assembly through an opening in the side of the tip.

In an alternate embodiment, the guiding catheter is advanced into the target area of the myocardium until it abuts with the myocardial wall where the cellular material is to be deployed. The guiding catheter may be equipped with prongs or anchors at the end to secure the guiding catheter to the myocardial wall. Alternatively, in order to prevent misalignment of the needle assembly relative to the wall, the guiding catheter may include sensors for determining when the end of the guiding catheter is engaged and substantially flush with respect to the myocardial wall. In this manner, the cellular implants can be planted at the appropriate depths and with the appropriate spacing between adjacent implants.

In a second alternate embodiment, the cellular materials in liquid form are injected into the myocardial wall by means of a needle catheter suitable for injecting liquid.

BRIEF DESCRIPTION OF THE DRAWINGS

The invention is illustrated in the drawings in which like reference characters designate the same or similar parts throughout the figures of which.

DESCRIPTION OF THE PREFERRED EMBODIMENTS

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
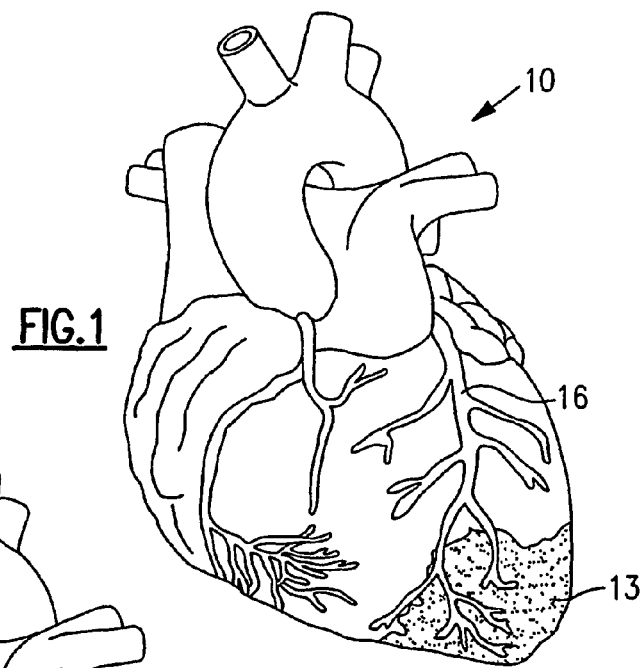
FIG. 1 is a perspective view of a heart having a damaged area in the myocardium.

In FIG. 1, a heart 10 is shown having a damaged portion 13 where inadequate perfusion from the coronary artery 16 has led to damage to the heart muscle that results in diminished cardiac function and resulting morbidity.

Figure 2:
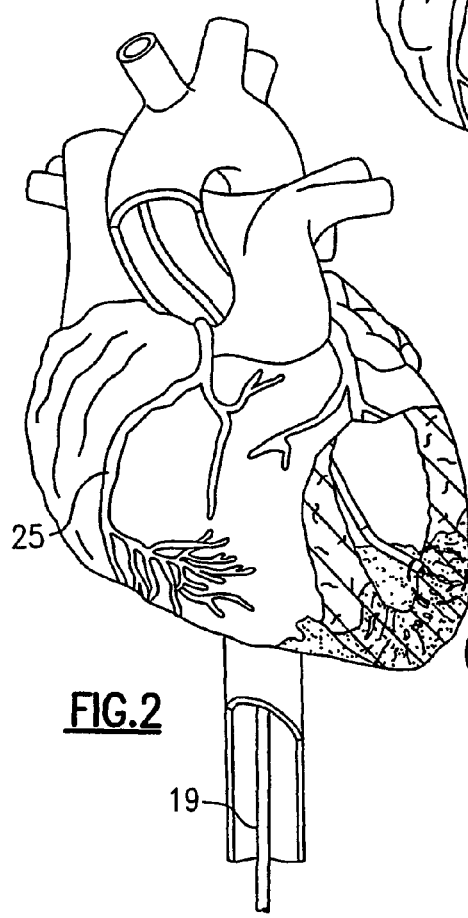
FIGS. 2-2A are perspective views of the heart undergoing the procedure of the present invention.

Turning to FIG. 2, the device and method of the present invention provides for catheter-based deployment is of a cellular material 22 having a combination of cellular and pharmacological materials for regenerating heart muscle damaged from cardiac arrest or coronary disease, improving cardiac function, and stimulating angiogenesis in the muscle wall. A guiding, articulating catheter 19 is shown introduced through the aorta 12 and traversing through the aortic arch 14 and down into the heart 10. As shown the catheter 19 implants the cellular material 22 directly into the heart muscle wall 25.

The preferred imaging system for the present invention includes a Toshiba/Acuson digital color echo to create visualization of the damaged myocardium. A fluoroscope allows visualization of the catheterization and needle penetration into the myocardial wall. An ECG creates a short potential voltage change (PVC) when the needle enters the wall which indicates to the interventionist that the needle has entered the myocardial wall. A monophasic action potential mapping probe at the tip of the guide catheter is able to distinguish viable tissue from non-viable tissue at the cellular level by measuring membrane potentials, NA, P, CA, and the like. The tip of the guide catheter also includes a surface flush probe. The probe assures that the tip is flush with the myocardium wall for the proper injection angle. A box visible to the interventionist lights up when the probe is flush with the myocardial wall which indicates that it is the appropriate time to inject.

Also, ECG electrodes are positioned on the curve of the guide catheter to measure the electrical activity of the heart.

LocalLisa™ software creates a colorized electro-magnetic map of the heart using standard ECG electrode guide catheters.

Saadat™ software overlays on the fluoroscope screen to show where injections have been made in muscle. A tilt view allows 3-D visualization.

The above described elements in combination provide a preferred imaging system for use in heart muscle regeneration procedures of the type disclosed in the present invention.

Figure 3:
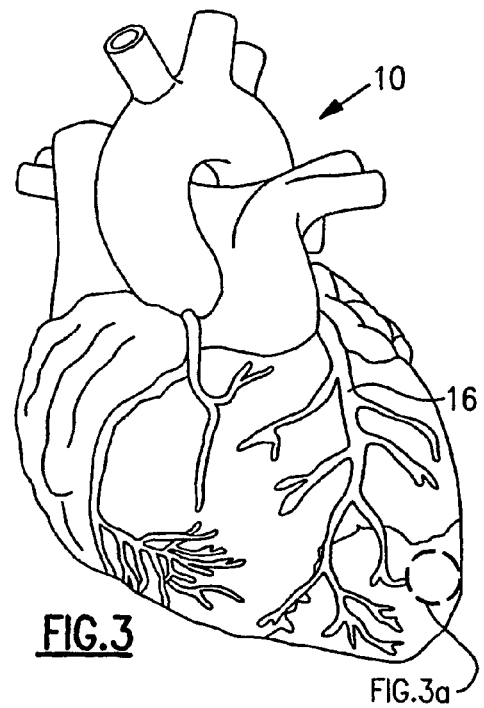
FIGS. 3-3A are perspective views of the head after the damaged muscle tissue has been regenerated according to the method of the present invention.
Figure 2A:
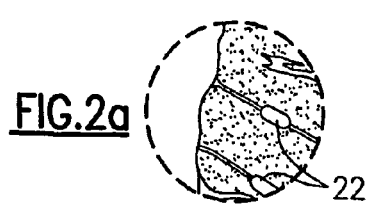
Figure 3A:
Figure 4:
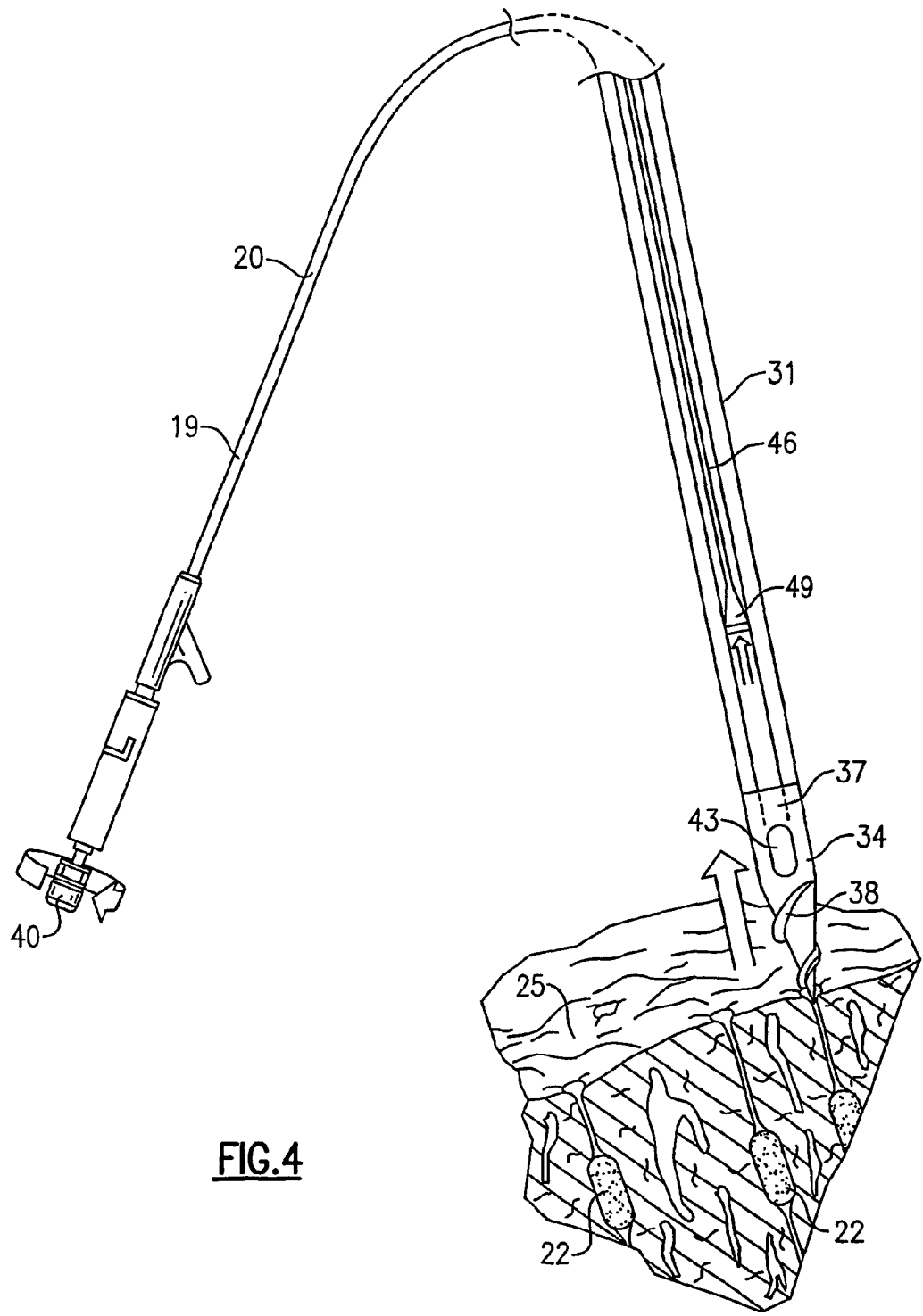
FIG. 4 is a perspective view of the deployment system of the present invention.
Figure 5:
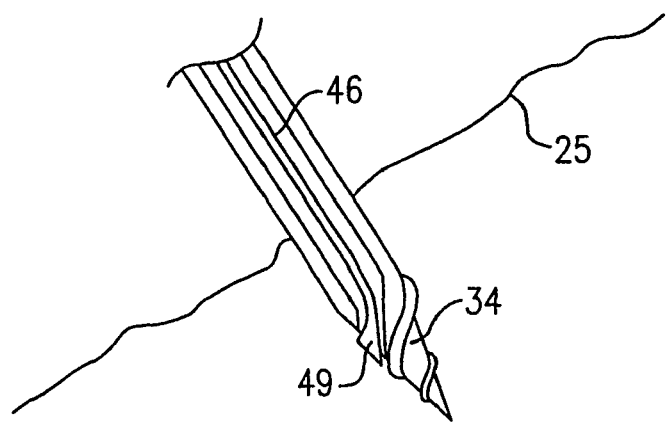
FIG. 5 is an enlarged detail view of the tip of the needle assembly of the present invention with the push rod plunger passing through the opening in the side of the needle assembly.
Figure 6:
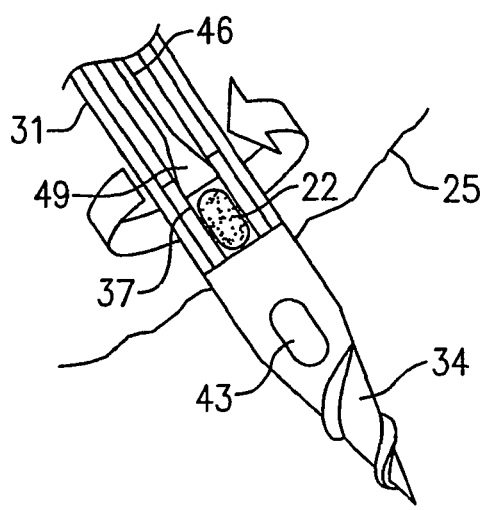
FIG. 6 is an enlarged detail view of the tip of the needle assembly of the present invention prior to ejection of the cellular material.
Figure 7:
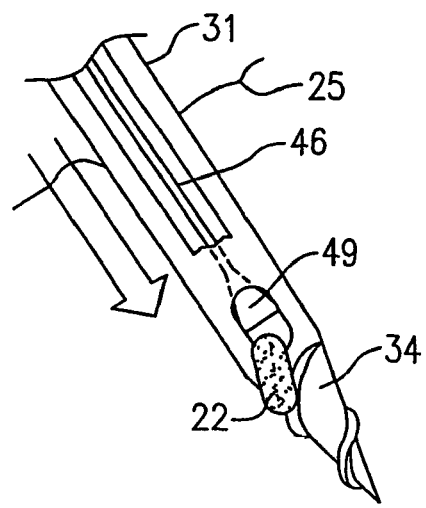
FIG. 7 is an enlarged detail view of the tip of the needle assembly of the present invention during ejection of the cellular material.

Turning to FIG. 3, the damaged area 13 of the myocardial wall has been repaired by the device and method of the present invention and the result is healthy muscle tissue capable of significantly increasing cardiac function.

In FIGS. 4-7, a catheter-based system including the guiding catheter 19 provides for deployment of the cellular material 22. The guiding catheter 19 is a standard 7-9 FR guiding catheter with a Teflon coated inner lumen 20. A needle assembly 31 having a needle tip 34 with a material cradle 37 is navigated up the central lumen 20 of the guiding catheter 19. The needle assembly 31 is pushable inside the guiding catheter 19 such that the needle tip 34 can be inserted into the heart muscle wall 25. The needle tip 34 is preferably pointed at the end for piercing the heart muscle wall 25. The tip 34 may be provided with a set of external threads 38 to aid in advancing the catheter 31 through the muscle by rotating the catheter 31 as it is pushed forward. The external threads 38 provide several advantages. The threads 38 create a greater injury response which serves to release more growth factors and thus creates more and larger angiogenic micro vessels. Compared to laser and straight needle, the external threads 38 had an approximately 5:1 improvement in vascular density. Also the external threads 38 trap thrombus which releases signals for release of growth factors and thus creates improved angiogenic response compared to clean holes and perfused thrombus with blood supply from LV.

Also, the external threads 38 stabilize the depth position for injections into the myocardium due to the resistance created by the threads. In contrast a straight needle tends to bounce in and out of the myocardium with each beat of the heart and accordingly, the depth of the injection is unpredictable. Accordingly, the needle assembly 31 is capable of being both pushed and twisted to advance the tip 34 into the heart muscle wall 25 by a hand operated wheel 40 operated by the interventionist (not shown) within a cavity of or outside of the body. As a result, the tip 34 carries the cradle 37 into the heart muscle wall.

In operation, the guiding catheter 19 is deployed to the myocardial wall 25 through percutaneous entry and guidance through the vasculature through techniques known to those of ordinary skill in the art. The catheter 19 may be introduced, for example, through the femoral artery and then passed through the aorta and the aortic arch and into the heart wall 25. Other routes such as the brachial arteries are also available. The guiding catheter 19 is preferably provided with a soft tip to facilitate guidance through the vasculature. Once the catheter 19 reaches the target area of the myocardium, the needle assembly 31 is pushed forward until the sharp tip 34 engages with the myocardial wall 25. If the sharp tip 34 is equipped with the external screw-type thread 38, the needle assembly 31 is pushed and rotated such that the needle assembly 31 enters the myocardial wall 25. The external threads 38 provide for entry into the myocardium with control. Pushing action, which can be dangerous, is minimized. A simple slow turn creates stable controlled entry into the myocardium. A straight needle requires strong pressure to break the surface tension and is relatively difficult to control the depth and the angle within the myocardium. Once the needle assembly 31 has been advanced into the myocardial wall 25 a predetermined distance, the push wire 46 is extended such that the platform 49 extends out of the cradle 37 through opening 43 and into the heart wall 25. The platform 49 is pressed into the heart wall 25 and then removed in a reciprocating motion to create a "divot" like indentation in the heart muscle wall. The "divot" provides a pocket for cells and increases the cell retention compared to the straight needle design. With the straight needle design, the cells tend to migrate up the capillaries and out of the coronary veins since that is the path of least resistance. The push wire 46 can be used to create a large pocket for cell retention as described above and can also be used to cauterize or close capillaries to improve cell retention in the myocardium. Mechanical closing of capillaries is done by packing tissue density with a rounded tip at the end of the push wire 46 which exits through opening 43 into the myocardium.

Next, the platform 49 is removed from catheter 31 by retracting push wire 46. The platform 49 is retracted so that a material 22 can be inserted into catheter 31 in front of the platform 49. In a like manner, the platform 49 can be retracted such that access to a liquid injection through a stop cock is provided, and then the liquid is injected through catheter 31 toward opening 43 in tip 34.

Once the material 32 has been deployed to its position inside the myocardial wall, the push rod 46 and platform 49 are then held against the material 22 while the tip 34 of the needle assembly 31 is retracted from the myocardial wall 25. The needle assembly 31 is then completely removed from the wall 25 leaving the cellular material 22 implanted in the heart muscle wall 25. The needle assembly 31 is then removed through the guiding catheter 19 and the percutaneous entry site is closed and treated according to standard techniques.

Figure 8:
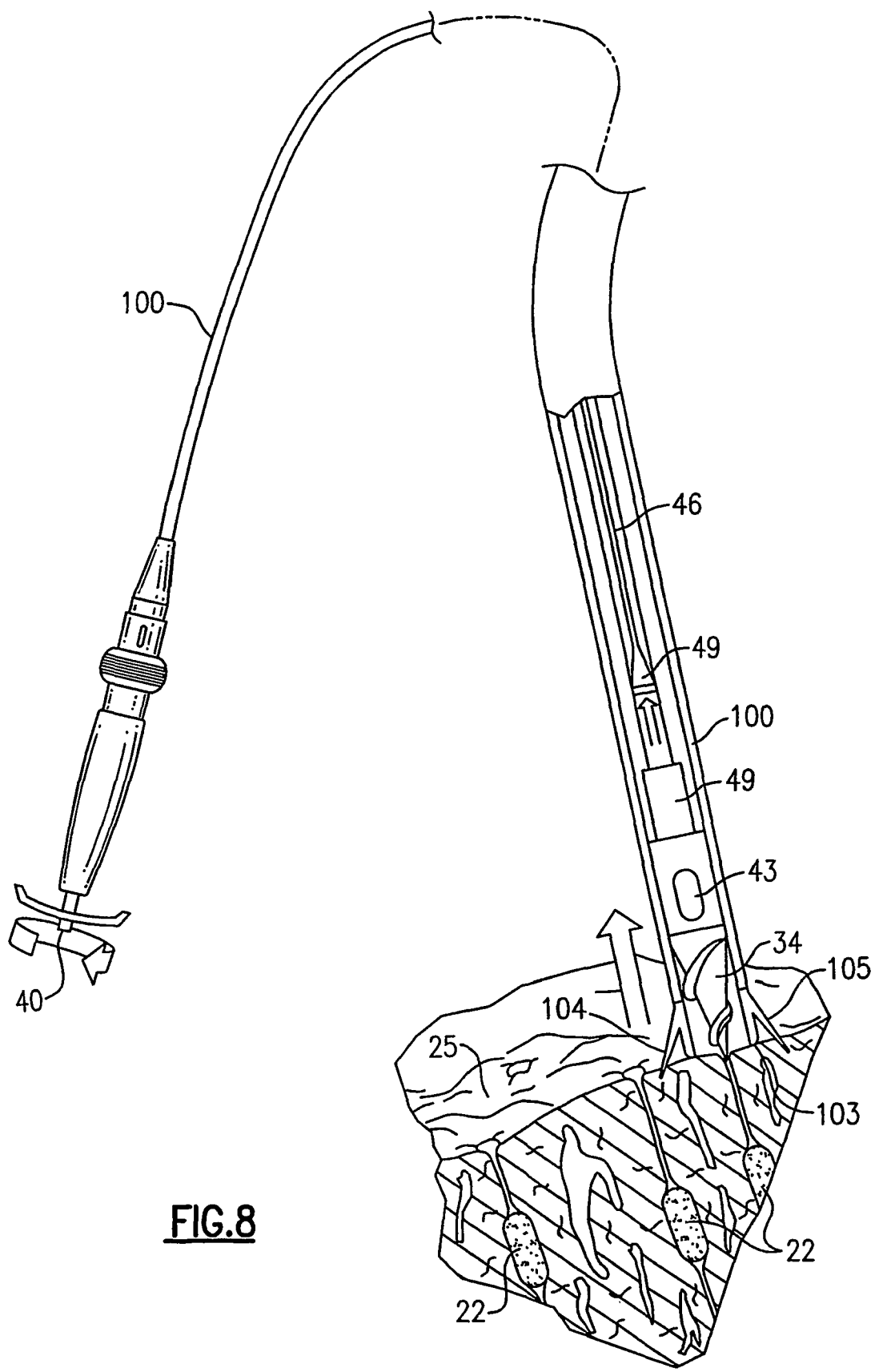
FIG. 8 is an alternate embodiment of the deployment system of the present invention.

Turning to FIG. 8, an alternate embodiment of the deployment system includes a guiding catheter 100 having an outer wall 103 that is designed to engage directly with the heart muscle wall 25. The guiding catheter 100 may be equipped with hooks 104 or anchors for penetrating the heart muscle wall 25 to hold the guiding catheter 100 in position against the heart muscle wall 25. The positioning of the catheter-based system with respect to the heart muscle wall 25 is important to achieve the desired positioning, spacing and depth for adjacent cellular materials 22. Accordingly, control of the entry point of the individual cellular materials 22 is important. If the guiding catheter 100 becomes misaligned with the heart muscle wall 25 the needle assembly 31 may enter the heart wall 25 at an angle that causes either too much or too little space between adjacent materials 22. In order to control the dosage of the drugs and the amount of cellular material per area of muscle, the entry point of the needle assembly 31 has to be controlled. Also, if the needle assembly 31 enters at the wrong angle with respect to the myocardial wall 25, the proper depth may not be achieved and the material 22 may not remain implanted in the heart wall 25.

Accordingly, the end of the guiding catheter 100 may be equipped with hooks 104 or other anchoring devices to grip the heart wall 25 to maintain the proper position of the catheter-based system relative to the heart wall 25. Alternatively, an opto-electric or other type of sensor 105 may be provided at the end of the guiding catheter 100 to ensure that the end of the guiding catheter 100 is substantially in the proper alignment with the heart wall 25. The sensor 105 can determine if both sides of the end of the guiding catheter 100 are engaged with the heart wall 25 such that the needle assembly 31 enters the heart wall 25 substantially perpendicular thereto and will not enter at a misaligned incident angle that could lead to the problems discussed above.

Figure 9A:
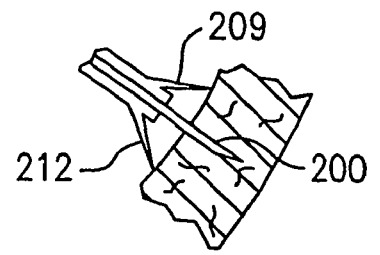
FIGS. 9-9A-9B are alternate embodiments of the deployment system of the present invention; and, FIG. 10 is a front elevational view of a needle assembly equipped with an auxiliary wire.
Figure 9B:
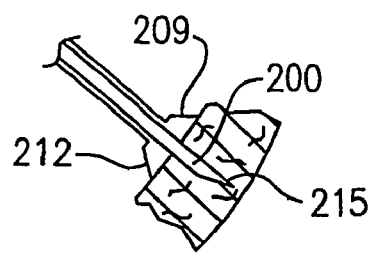
Figure 9:
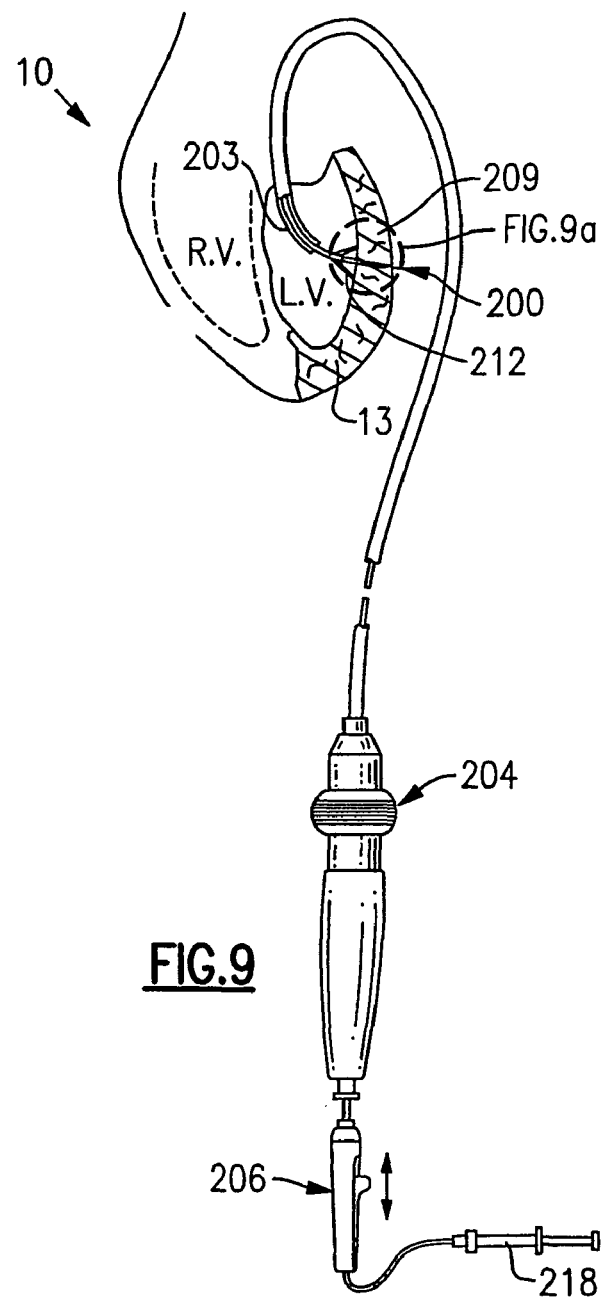

Turning to FIG. 9, a needle-based deployment system is shown. A needle 200 is capable of being deployed through a deflecting guiding catheter 203 operated by a wheel 204 as known to those of skill in the art. Once the needle 200 is carried to the intervention site by means of the catheter 203, the needle 200 is displaced axially relative to the catheter 203 by a thumb-operated advancer 206 in a push rod configuration as known to those of ordinary skill in the art.

The needle 200 is preferably 16 gauge, however, other sizes may also be suitable. As shown, the needle 200 penetrates the heart muscle wall to a predetermined depth. The depth is determined by a pair of mechanical stops 209, 212 disposed on opposite sides of the needle 200. The stops extend laterally with respect to the tip 215 of the needle 200 and are non-penetrating such that the interventionist is provided with an indication of when the needle 200 has been inserted to the proper depth. The needle 200 is fed by a syringe 218 with liquid forms of the cellular compositions set forth previously in connection with the pelletized cellular materials described above.

Figure 10:
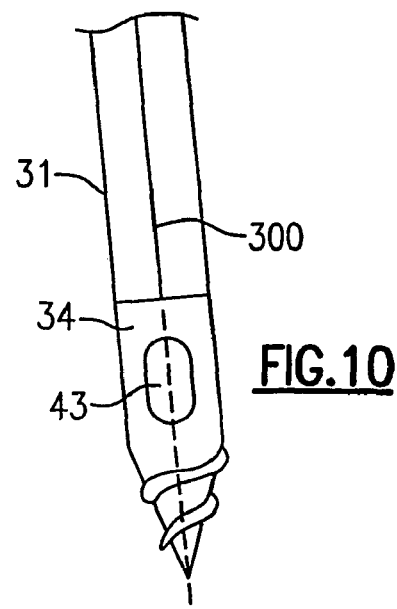

In FIG. 10, an auxiliary wire 300 is shown. Because the procedure of the present invention is performed while the heart is beating, it is important to locate the guiding catheter against the heart muscle wall at the beginning of the procedure and it is sometimes difficult to do so when the heart is moving. The thin axially disposed auxiliary wire 300 is capable of being pushed forward through the center of catheter (e.g. needle assembly) 31 such that the end of wire 300 can be inserted into the heart muscle wall to anchor or position the needle assembly 31 relative to the heart muscle wall prior to entry of the tip 34 into the muscle wall. Accordingly, auxiliary wire 300 functions as a guide wire and anchor to aid in bringing the needle assembly 31 against the moving heart muscle wall. Without the leading wire 300, the guiding catheter 31 may be "bounced" off of the moving wall and may be more difficult to locate.

It is to be understood that although the present invention has been described in connection with percutaneous procedures, it is also suitable for open chest cavity procedures where the interventionist has detected heart muscle damage during the open procedure. Also, although the present invention has been described in connection with the myocardium, the cellular material and deployment system is not to be limited to use only with the heart muscle wall and may be applied to other organs of the body with suitable cellular compositions formulated for use in other areas.

The device of the present invention can be used for delivery of compositions into heart muscle damaged from cardiac arrest or coronary disease for the purpose of improving cardiac function and/or stimulating angiogenesis.

The cellular compositions of the present invention may comprise any type of myogenic cells. Further, the composition may also have angiogenic growth factors, support matrix materials or pharmacological agents. The composition may be formulated into a liquid, slurry or paste, pellet or a porous ceramic material.

Myogenic cells suitable for the present invention include cells such as, but not limited to, skeletal myoblasts, embryonic stem cells, mesenchymal stem cells or combinations thereof. Skeletal myoblasts may be autologous or allogenic. In a preferred embodiment, the cells are derived from the same individual (autologous). A method for culturing, selecting and implanting skeletal myoblasts into host muscles is described in U.S. Pat. No. 5,130,141 to Law et al. Embryonic stem cells may be obtained by any method well known to those skilled in the art. An example of such a method can be found in U.S. Pat. Nos. 6,090,622 and 6,245,566 to Gearhart et al. Mesenchymal stem cells can be induced to differentiate into various cell types, including muscle cells. Mesenchymal cells can be obtained as described in U.S. Pat. No. 5,486,359 to Caplan et al. It is preferable to use skeletal myoblasts since these cells are already committed to becoming muscle cells and are relatively resistant to ischemia. Further, myoblasts can readily be cultured from a muscle biopsy.

Angiogenic growth factors are useful agents for promoting the growth of new blood vessels. Angiogenic growth factors include a variety of known growth factors such as fibroblast growth factors (FGFs), particularly basic FGF (βFGF) and acidic FGF (αFGF); epidermal growth factor (EGF); platelet-derived growth factor (PDGF); vascular endothelial growth factor (VEGF); and the like. Such agents can prompt the growth of new blood vessels. Accordingly, in the present invention these growth factors can be used in the implantation composition to enhance the growth of new blood vessels so as to supply nutrients to the heart muscle.

Support matrix materials can be selected so as to achieve the desired viscosity and porosity. Thus, the cellular and non-cellular components may be prepared in a aqueous medium. In one embodiment, the composition may contain fibrin glue. Fibrin glue comprises thrombin and cryoprecipitate. The fibrin GLUE helps to adhere the implanted materials to the site of injection so as to reduce cell loss.

The cellular compositions for implantation may also contain pharmacological agents such as pyruvate. Pyruvate is a natural, nontoxic chemical compound found in the body and which when combined with adrenaline-like catecholamine drugs has been shown to improve cardiac function.

In one embodiment, cultured stem cells or myoblasts are transfected with a nitric oxide synthase gene prior to inclusion in the implantation composition. It is known that nitric oxide plays a role in regulating blood pressure and the clotting of blood. Procedures for transfecting cells are known to those skilled in the art (for example, see U.S. Pat. No. 6,149,936 and references therein).

In the case of a porous ceramic delivery system, a porous ceramic that is biodegradable and thus eventually removed and eliminated via natural agencies is preferably used. The porous ceramic may constitute a porous sintered, porous vitreous, or porous glass-like, physiologically acceptable, biodegradable alkali metal salt, alkaline earth metal salt, or transition metal salt. For example, physiologically acceptable, biodegradable salts include but are not limited to the phosphates, sulfates, carbonates, and silicates of sodium, potassium, calcium, magnesium, manganese, vanadium, iron, copper, zinc, silver, gold, platinum, aluminum, cobalt and the like. The salts are sintered to reduce their solubility in body fluids causing a corresponding reduction in their chemical activity so that the porous ceramic is tolerated in the body and acute inflammatory reactions are avoided. A preferred ceramic is sintered calcium phosphate, preferably tricalcium phosphate (TCP). An especially preferred ceramic phosphate is beta tricalcium phosphate (BTCP) having a Ca/P ration of about 1.5. Porous ceramic for purposes of this invention means any of the foregoing salts that are formed into a sintered or ceramic mass having pores suitable for containing effective amounts of myogenic cells.

The method for preparing the porous ceramic delivery system of the present invention, e.g., implant material, comprises introducing a physiologically acceptable biodegradable porous ceramic such as sintered tricalcium phosphate to an aqueous solution of the cellular materials described above and causing the cellular mixture to become entrapped in the ceramic's pores by evaporating the solvent, freeze drying it, or otherwise allowing the ceramic to absorb the cellular mixture, which will form the desired system. The preferred weight ratios of porous ceramic to cellular mixture is a range of at least 1:100 to about 1:1. Effective dosages of other components of the implantation composition are determined by the characteristics of the recipients and the objective of the treatment. The porous ceramic delivery system may be preformed by placing the powdered salts into a mold of the desired shape for implantation, and then firing the salt in a kiln or electric furnace to sinter the salt or otherwise convert it to a solid, unitary porous mass. Generally this method forms the active delivery system of the invention. Additives or supplements may be included in the admixture with the cellular mixture and porous ceramic, each for its own particular function. In preferred embodiments, the biodegradable porous ceramic delivery system is formed into a rod, plate, flake or otherwise shaped as desired.

The porous ceramic materials could be used in combination with the myogenic cells, growth factors, other materials such as a biopsy of skeletal bone tissues, a biopsy of skeletal bone tissue mixed with a biopsy of healthy heart muscle, pyruvate, catecholamine stimulating agents, fibrin glue, or combinations thereof.

An illustration of a suitable cellular implantation composition is as follows: by volume 60-90% (preferably 80%) differentiated embryonic stem cells, 5-20% (preferably 10%) growth factors, 1-10% (preferably 2%) pyruvate, 1-10% (preferably 2%) fibrin glue and 1-10% (preferably 1%) catecholamine stimulating drugs.

Various embodiments of the cellular implantation compositions of the present invention are provide below. These compositions are presented only for illustrative purposes and not to be construed as restrictive.

Composition #1, mesenchymal stem cells differentiated to become cardiomyocyte-like, such cells being transformed with a gene encoding nitric oxide synthase, and vascular endothelium growth factors,.

Composition #2, cultured embryonic stem cells differentiated to become cardiomyocyte-like, FGF and VEGF growth factors, fetal endothelial cells, placenta cord blood, and pyruvate.

Composition #3, cultured skeletal muscle cells, fetal endothelial cells, fibroblast and vascular endothelium growth factors, and pyruvate. The cells may be transfected with a gene encoding nitric oxide synthase.

All of the above compositions may also include catecholamine stimulating drugs and other cardiac output stimulating drugs. Also, aspirin and Aldacatone can be added to the compositions An illustrative cellular composition comprises the following:

About 50 million slow twitch myoblasts in about 0.2 cc of human albumin transfected with cDNA encoding Nitric Oxide Synthase; Angiopoiten 1 Tie Receptors ("Ang 1"); L-Arginine; and VEGF and FGF.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. A deployment system for a myocardial cellular material, comprising:
    a guiding catheter having at least one lumen defined therein;
    a needle assembly capable of sliding through the lumen of the guiding catheter, the needle assembly having a lumen defined therein and terminating in a tip, the tip having at least one side, the needle assembly having an opening in the at least one side of the tip disposed in communication with the lumen of the needle assembly so that the myocardial cellular material can be deployed into a myocardial wall from inside the lumen of the needle assembly;
    a push rod having a platform disposed at its distal end, the rush rod disposed inside the lumen of the needle assembly; and
    an anchor wire disposed axially through the tip and capable of engaging with a portion of the myocardial wall to position the needle assembly relative to the myocardial wall,
    wherein the guiding catheter has an outer wall having a distal end, wherein the distal end comprises a sensor and forms an anchor extending frontwardly so as to hold the guiding catheter in a position against the myocardial wall.

2. A deployment system for a myocardial cellular material, comprising:
    a guiding catheter having at least one lumen defined therein;
    a needle assembly capable of sliding through the lumen of the guiding catheter, the needle assembly having a lumen defined therein and terminating in a tip, the tip having at least one side, the needle assembly having an opening in the at least one side of the tip disposed in communication with the lumen of the needle assembly;
    a push rod having a platform disposed at its distal end, the push rod disposed inside the lumen of the needle assembly; and
    an anchor wire disposed axially through the tip and capable of engaging with a portion of a myocardial wall to position the needle assembly relative to the myocardial wall,
    wherein the guiding catheter has an outer wall having a distal end, wherein the distal end forms an anchor extending frontwardly so as to hold the guiding catheter in a position against the myocardial wall.

3. A method of deploying a myocardial cellular material, comprising:
    providing a guiding catheter having at least one lumen defined therein and a needle assembly capable of sliding through the lumen of the guiding catheter, the needle assembly having a lumen defined therein and terminating in a tip, the tip having at least one side, the needle assembly having an opening in the at least one side of the tip disposed in communication with the lumen of the needle assembly so that the myocardial cellular material can be deployed into a myocardial wall from inside the lumen of the needle assembly;
    advancing the guiding catheter through a patient's body to the myocardial wall and utilizing an anchor wire disposed axially through the tip as a guidewire to engage the myocardial wall and position the needle assembly relative to the myocardial wall, wherein the guiding catheter has an outer wall having a distal end, wherein the distal end forms an anchor extending frontwardly so as to hold the guiding catheter in a position against the myocardial wall;
    deploying the needle assembly by inserting the tip of the needle assembly into the myocardial wall to a predetermined depth;
    extending a push rod having a platform through the opening in the side of the tip and engaging the platform directly with the myocardial wall;
    retracting the platform and inserting the myocardial cellular material into the lumen of the needle assembly; and
    deploying the myocardial cellular material into the myocardial wall through the opening in the side of the tip.

4. The method of claim 3, wherein the platform is disposed at the distal end of the push rod.

5. The method of claim 3, wherein the tip of the needle assembly has a point at its distal end.

6. The method of claim 3, wherein the guiding catheter is capable of articulating.

7. The method of claim 3, wherein the needle assembly is capable of articulating.

8. The method of claim 3, wherein the tip has an outer surface with a set of external threads disposed thereon.

9. The method of claim 3, wherein the guiding catheter further comprises a distal end having an anchor hook extending therefrom.

10. The method of claim 3, wherein the guiding catheter further comprises a distal end having a sensor.

11. The method of claim 3, wherein the sensor is an optoelectric sensor.

12. The method of claim 3, wherein the needle assembly has a cradle for holding a charge of the myocardial cellular material, the cradle disposed between the lumen in the needle assembly and the opening in the side of the tip.

* * * * *